United States Patent
Rhodes

(10) Patent No.: US 6,867,047 B2
(45) Date of Patent: Mar. 15, 2005

(54) METHOD AND APPARATUS FOR PREVENTING NITROGEN INTERFERENCE IN PYRO-ELECTROCHEMICAL METHODS

(75) Inventor: John R. Rhodes, Austin, TX (US)

(73) Assignee: Spectro Analytical Instruments, Marble Falls, TX (US)

( * ) Notice: Subject to any disclaimer, the term of this patent is extended or adjusted under 35 U.S.C. 154(b) by 4 days.

(21) Appl. No.: 10/055,726

(22) Filed: Jan. 23, 2002

(65) Prior Publication Data

US 2003/0049855 A1 Mar. 13, 2003

Related U.S. Application Data

(63) Continuation-in-part of application No. 09/951,760, filed on Sep. 11, 2001.

(51) Int. Cl.[7] .............................................. G01N 33/00
(52) U.S. Cl. ...................... 436/118; 436/116; 436/117; 436/155; 436/159; 436/160; 422/78
(58) Field of Search ..................... 436/116–118, 119, 436/120, 155, 159, 160; 422/78

(56) References Cited

U.S. PATENT DOCUMENTS

| | | | |
|---|---|---|---|
| 3,622,488 A | 11/1971 | Chand et al. | 204/195 |
| 3,650,696 A | 3/1972 | Eads | 23/230 |
| 3,795,812 A | 3/1974 | Okabe | 250/373 |
| 3,838,969 A | 10/1974 | Dugan | 23/230 |
| 3,840,341 A | * 10/1974 | Rogers | 436/146 |
| 3,894,419 A | 7/1975 | Mator et al. | 73/1 |
| 3,925,332 A | 12/1975 | Naito et al. | 260/79.3 |
| 3,976,450 A | 8/1976 | Marcote et al. | 55/158 |
| 4,004,882 A | 1/1977 | Byrne et al. | 23/254 |
| 4,018,562 A | 4/1977 | Parks et al. | 23/230 |
| 4,066,409 A | 1/1978 | Fine | 23/230 |
| 4,070,155 A | 1/1978 | Fraim | 23/230 |
| 4,077,774 A | 3/1978 | Neti et al. | 23/232 |
| 4,172,705 A | 10/1979 | Castro et al. | 23/230 |
| 4,223,324 A | 9/1980 | Yamamori et al. | 346/140 |

(List continued on next page.)

FOREIGN PATENT DOCUMENTS

| | | |
|---|---|---|
| GB | 2017315 | 10/1979 |
| GB | 1578281 | 11/1980 |
| GB | 2049952 | 12/1980 |
| GB | 2319606 | 6/1996 |
| WO | WO 94/07134 | 3/1994 |
| WO | WO 95/22049 | 8/1995 |
| WO | WO 99/18430 | 4/1999 |
| WO | WO 99/58950 | 11/1999 |
| WO | WO 01/46683 A2 | 6/2001 |

OTHER PUBLICATIONS

Liu "Molybdenum carbide as catalyst for conversion of nitrogen dioxide to nitric oxide", Huanjing Huaxue, 1986, v. 5, No. 6, pp. 30–33 (Abstract).*

(List continued on next page.)

*Primary Examiner*—Yelena G. Gakh
(74) *Attorney, Agent, or Firm*—Vinson & Elkins L.L.P.

(57) ABSTRACT

Methods and apparatus are described for preventing nitrogen interference in the detection of a substance. In particular, it relates to new methods and apparatus for preventing interference due to nitrogen in pyro-electrochemical methods for measuring substances, for example sulfur content, contained within liquids such as petroleum products and beverages. One preferred apparatus and method comprises a catalytic converter or thermal converter to selectively remove the nitrogen-containing interferant, for example $NO_2$, in the pyrolyzed gas stream to NO without affecting the sulfur content. A second preferred apparatus and method comprises a chemical scrubber to selectively remove the nitrogen-containing interferant from the gas stream without affecting the sulfur content.

10 Claims, 5 Drawing Sheets

U.S. PATENT DOCUMENTS

| | | | |
|---|---|---|---|
| 4,257,772 A | 3/1981 | Bognin et al. | 23/230 |
| 4,257,777 A | 3/1981 | Dymond et al. | 23/232 |
| 4,272,248 A | 6/1981 | Neti | 23/232 |
| 4,293,308 A | 10/1981 | Sisti et al. | 23/230 |
| 4,301,114 A | 11/1981 | Rounbehler et al. | 422/52 |
| 4,330,298 A | 5/1982 | Hawn et al. | 23/230 |
| 4,332,591 A | 6/1982 | Oi et al. | 23/230 |
| 4,351,801 A | 9/1982 | Bartke | 422/78 |
| 4,352,779 A | 10/1982 | Parks | 422/52 |
| 4,401,763 A | 8/1983 | Itoh | 436/115 |
| 4,409,336 A | 10/1983 | Oita | 436/123 |
| 4,467,038 A | 8/1984 | Scott | 436/115 |
| 4,587,003 A | 5/1986 | Tantram et al. | 204/412 |
| 4,633,021 A | 12/1986 | Hanes | 568/454 |
| 4,633,704 A | 1/1987 | Tantram et al. | 73/23 |
| 4,678,756 A | 7/1987 | Parks | 436/123 |
| 4,765,961 A | 8/1988 | Schiff et al. | 422/52 |
| 4,766,760 A | 8/1988 | Poshemansky et al. | 73/23.1 |
| 4,778,764 A | 10/1988 | Fine | 436/116 |
| 4,843,016 A | 6/1989 | Fine | 436/106 |
| 5,152,963 A | 10/1992 | Wreyford | 422/80 |
| 5,227,135 A | 7/1993 | Godec et al. | 422/98 |
| 5,310,683 A | 5/1994 | Godec et al. | 436/123 |
| 5,330,714 A | 7/1994 | Godec et al. | 422/52 |
| 5,395,501 A | 3/1995 | Rohrbacker et al. | 204/265 |
| 5,397,708 A | 3/1995 | Lessard et al. | 436/30 |
| 5,409,591 A | 4/1995 | Baker et al. | 204/425 |
| 5,424,217 A | 6/1995 | Benner et al. | 436/123 |
| 5,466,350 A | 11/1995 | Baker et al. | 204/153.14 |
| 5,501,981 A | 3/1996 | Ray et al. | 436/123 |
| 5,580,433 A | 12/1996 | Baker et al. | 204/425 |
| 5,614,417 A | 3/1997 | Kubala et al. | 436/120 |
| 5,632,875 A | 5/1997 | Chapples et al. | 204/431 |
| 5,661,036 A | 8/1997 | Benner et al. | 436/123 |
| 5,668,302 A | 9/1997 | Finbow et al. | 73/23.2 |
| 5,916,523 A | 6/1999 | Yan et al. | 422/83 |
| 5,935,519 A | 8/1999 | Benner et al. | 422/52 |
| 6,013,530 A | 1/2000 | Tawara | 436/123 |
| 6,057,162 A | 5/2000 | Rounbehler et al. | 436/119 |
| 6,130,095 A | 10/2000 | Shearer | 436/123 |
| 6,143,245 A | 11/2000 | Yan et al. | 422/52 |

OTHER PUBLICATIONS

"Standard test method for total trace nitrogen and its derivatives in liquid aromatic hydrocarbons by oxidative combustion and electrochemical detection," American Society for Testing and Materials, Designation: D 6366–99, 1999.

"Test method for total sulfur in liquid aromatic hydrocarbons and their derivatives by oxidative combustion and electrochemical detection," American Society for Testing and Materials, Designation: D 6428–99, 1999.

"Standard test method for trace nitrogen in liquid petroleum hydrocarbons by syringe/inlet oxidative combustion and chemiluminesence detection," The American Society for Testing and Materials, Designation: D 4629–96.

"Standard test method for determination of total sulfur in light hydrocarbons, motor fuels and oils by ultraviolet fluorescence," The American Society for Testing and Materials, Designation: D 5453–93.

Frontijn, et al., "Homogenous chemiluminescent measurement of nitric oxide with ozone," *Analytical Chemistry*, vol. 42, No. 6, 575–79, May 1970.

Schwarz, et al., "Fluorescence detection of dulfur fioxide in air at the parts per billion level," *Analytical Chemistry*, vol. 46, No. 8, 1024–28 Jul. 1974.

EP 0127387 A2, 1984.
EP 0366262 A2, 1990.
GB 2323171, 1997.

\* cited by examiner

METHOD AND APPARATUS FOR PREVENTING NITROGEN INTERFERENCE IN PYRO-ELECTROCHEMICAL METHODS

CROSS REFERENCE TO RELATED APPLICATION

This application is a continuation-in-part of application Ser. No. 09/951,760 filed on Sep. 11, 2001, entitled A Method and Apparatus for the On-stream Analysis of Total Sulfur and/or Nitrogen in Petroleum Products.

FIELD OF THE INVENTION

The present invention relates to new methods and apparatus for preventing nitrogen interference in the detection of a substance. More specifically, it relates to new methods and apparatus for preventing nitrogen interference in pyro-electrochemical methods of analysis if a substance through the selective conversion and/or removal of certain nitrogen-containing interfering gases.

BACKGROUND OF THE INVENTION

Sulfur in motor fuels such as gasoline and diesel fuel is an important pollutant. Its concentration has been regulated over the past several years so as not to exceed levels in the range of 500 parts per million (ppm). Recent government regulations worldwide will reduce the acceptable sulfur contents of gasoline and diesel fuel to below 50 ppm with specific regulatory levels set at 30 and 15 ppm, for example, to be enforced in the next two or three years. In order to ensure that the regulated concentration levels are not exceeded, petroleum products are subjected to both laboratory and on-stream analysis during their processing and production. Sulfur and nitrogen also occur at parts per million levels in beverages and likewise need to be monitored. Suitable methods for use at concentrations down to 10 ppm and below are "pyro-UV fluorescence" (ASTM D 5453) and "pyro-electrochemical" (ASTM D 6428) methods, each method incorporated herein by reference. Nitrogen often occurs in petroleum products and (incidentally) can be measured by "pyro-chemiluminescence" (ASTM D4629) or "pyro-electrochemical" (ASTM D 6366) methods, each method incorporated herein by reference. In all these methods, a small fixed volume of sample is thermally oxidized ("pyrolyzed") and the combustion products are analyzed for $SO_2$ or NO. The concentrations of these gases are measured by either UV fluorescence spectrometry ($SO_2$), chemiluminescence (NO), or by electrochemical detectors specific for $SO_2$ or NO.

According to the ASTM method directed toward pyro-electrochemical techniques, a fixed volume, usually 5–20 microliters, of liquid sample is injected into the pyrolyzer along with an inert carrier gas, usually argon at a flow rate of about 130–160 sccm (standard cubic centimeters per minute) and including some oxygen, about 10–30 sccm. The liquid vaporizes and then reaches the combustion zone where another flow of oxygen, about 450–500 sccm, the "pyrolysis-gas", is introduced and effects complete thermal oxidation at about 1050° C. The reactor is a quartz tube heated by a tube furnace. The flow rate of liquid sample should never exceed about 4 µl/s (microliters/second), otherwise the combustion process will be starved of oxygen and soot formation (or "sooting") will occur, that is, the internal surfaces downstream of the hot zone will be covered with soot. The ASTM methods specify a flow rate of 1 µl/s. The gas output from the pyrolyzer is a mixture of the inert carrier gas (about 20 vol %), unconsumed oxygen (about 60 vol %), carbon dioxide ($CO_2$)(about 10 vol %), water vapor (about 10 vol %) and ppm levels of $SO_2$. The dewpoint is 45–50° C., so the gas lines are usually heat traced and/or the water vapor content is reduced to prevent condensation. Water vapor can be reduced without affecting the $SO_2$ content by means of a permeation dryer which operates on the principle of absorption-desorption of water vapor through a membrane. The conditioned gas mixture is then fed to the $SO_2$ detector. A typical 20 µl sample takes some 20 seconds to inject and passes through the pyrolyzer and other gas sample plumbing in about one minute. The $SO_2$ concentration at the detector starts at zero just before the injection, rises to a maximum and then falls off to zero. The rates of rise and fall depend on the various flow rates and gas mixing, and on any molecular exchange reactions that the $SO_2$ undergoes at surfaces with which it comes into contact with. The detector response ideally follows this same profile. The actual detector response will be less than ideal, so additional broadening of the time profile will occur. In practice, the whole $SO_2$ signal from a given injection will extend over 2–5 minutes. This signal is integrated and is directly proportional to the total amount of sulfur in the original sample. As long as the sample volume remains constant, the $SO_2$ signal is proportional to sulfur content of the original sample. "Continuous" analysis is accomplished by automating the sample injection procedure.

The electrochemical detectors have the great advantages of simplicity and low cost. However, the $SO_2$ sensor, while not sensitive to NO, is highly sensitive to any $NO_2$ in the pyrolyzed gas stream, having an $NO_2$ response equal to upwards of about −100% of the $SO_2$ response. The pyrolysis occurs in a quartz tube held at about 1050° C. in a tube furnace. At this temperature gas chemistry indicates that the thermal equilibrium between the nitrogen combustion products NO and $NO_2$ is almost completely driven toward about 100% NO, so production of $NO_2$ is not expected and was not mentioned in any of the relevant ASTM methods.

We have surprisingly and unexpectedly found that the $SO_2$ signal from diesel fuel, for example, containing about 50 ppm nitrogen and about 20 ppm sulfur is strongly suppressed compared to that from diesel containing about 20 ppm sulfur and about zero nitrogen. Part of the sulfur signal is reduced to zero or negative values and the sensor takes as much as one hour to recover after nitrogen in no longer present in the sample. FIG. 1 shows a typical effect. It appears that some of the NO is converted to $NO_2$ in the cooler parts of the pyrolysis tube where the thermal equilibrium favors more $NO_2$. Also, the electrochemical cell appears to be "poisoned" by the $NO_2$ with long-lasting effects. It is therefore desirable to prevent $NO_2$ from reaching the $SO_2$ detector.

SUMMARY OF THE INVENTION

Methods and apparatus are described below with special reference to their use in preventing nitrogen interference in laboratory and on-stream sulfur analyzers that employ thermal oxidation, that is pyrolysis, of a sample and electrochemical detection of sulfur-containing species, such as $SO_2$. However, the use of such techniques is not limited to this. These techniques can equally be employed to prevent interferences due to other gases, in analyzers for other constituents, such as nitrogen, in laboratory analyzers and on-stream analyzers that use other gas detectors. The methods and apparatus described are, however, limited to analysis techniques that employ thermal oxidation of the sample.

It is therefore an object of the present disclosure to provide for reproducible and reliable laboratory and/or on-stream pyro-electrochemical results by selectively converting and/or removing the interfering gases.

A further preferred feature of the present disclosure is to offer a method and/or apparatus in which the sulfur concentration of the analyzed gas stream is unaffected by the converter. One embodiment prefers that all surfaces "wetted" by the gas stream are inert to sub-parts per million concentrations of $SO_2$, at whatever temperature they must be to perform their function. Some preferred surface materials are composed of stainless steel or quartz. Especially preferred forms of stainless steel include 316 and 304.

Another object of the present disclosure is to keep the pressure drop through the converter minimal, preferably between about zero to about 10 inches of water, so that the quality of the pyrolysis is not deleteriously affected. In addition, pressure fluctuations are preferably kept to a minimum, preferably between about zero to about 10 inches of water, so as not to affect the response of the electrochemical cell.

An additional object of the present disclosure is that the highly enriched oxygen atmosphere of the analyzer gas stream (for example, in one embodiment, about 60% $O_2$, about 20% Ar, about 10% $CO_2$ and about 10% $H_2O$) preferably does not cause oxidation or combustion of the converter material at the converter operating temperature.

It is a further object of the present disclosure that the nitrogen-containing interferant, for example $NO_2$, is preferably about 100% removed from the analyzed gas stream by conversion to a gas species that does not affect the electrochemical detector, such as NO. A conversion efficiency of from about 90% to about 100% is preferred and an efficiency of greater than 96% is especially preferred.

A further object of the present disclosure is that the equilibrium of the $NO_2$ to NO reversible reaction (which favors $NO_2$ at low temperatures) is preferably "frozen" at about 0% to about 10% $NO_2$ by sufficiently rapid cooling of the analyzed gas stream output from the converter. Cooling the sample gas stream from the converter temperature of about 400° C. to ambient temperature in a period between about 0 to about 10 seconds is preferable and may be achieved by the normal gas flow rate of about 400 to about 800 standard cubic centimeters per minute (sccm) in the 0.25 inch outside diameter by 0.17 to 0.12 inch inside diameter tubing normally used for gas transport.

Another preferred feature of the present disclosure contemplates temperature control of the converter achieved, although not necessarily, by making the converter an integral part of the pyrolysis furnace that provides the pyrolysis temperature.

A further object of the present disclosure is that the conversion and/or removal means may be long-lasting, preferably requiring maintenance or replacement at intervals of not less than about one month and preferably of about one year or more.

One preferred embodiment of the present disclosure involves an method for removing nitrogen-containing interferants in pyro-electrochemical methods including the steps of thermally oxidizing a sample containing a substance for detection, for example sulfur-containing species which may be combusted to form $SO_2$, selectively removing a nitrogen-containing interferant from the sample gas, for example $NO_2$, cooling the sample gas after the selective removal step, and detecting the substance with an electrochemical detector. The selective removal may preferably be accomplished by removing the nitrogen-containing interferant using a scrubber or by selectively converting the nitrogen-containing interferant, for example $NO_2$, into a non-interfering species, for example NO. Converters and scrubbers have been used to segregate various gases in instrumentation for air analysis. For example, in chemiluminescence NOx analyzers, the chemiluminescent detector measures NO but is not sensitive to $NO_2$. A catalytic converter is employed to convert the $NO_2$ to NO, which it does quantitatively, so enabling the detector to measure NO plus $NO_2$, as NO. Stream switching is then employed to alternately bypass the converter, when just NO is measured. The $NO_2$ content is then calculated by measuring the difference between these values. These converters function by passing the sample gas stream through a bed of molybdenum, copper or carbon at a controlled temperature in the range 250° C. to 400° C. depending on the catalyst. A "thermal" converter can also be used which passes the gas through a stainless steel tube heated to about 900° C., at which temperature the thermal equilibrium between NO and $NO_2$ is driven to 100% NO. It is of course important to cool the output gas stream rapidly enough to "freeze" the chemical equilibrium at the 100% NO point achieved in the converter. The use of such converters in NOx analyzers does not require the $SO_2$ content of the gas stream to remain unaffected. Also, it is not known whether the conversion will work effectively in the highly enriched oxygen atmosphere of the pyrolysis exhaust. Another example of a converter is the use of either a heated tube or catalyst bed to convert $H_2S$ to $SO_2$, so that it can be measured by an $SO_2$ analyzer. A scrubber usually takes the form of a cartridge packed with selected chemicals. Scrubbers are used in air analysis instrumentation to remove unwanted gas species. For example a scrubber may be used to remove $SO_2$ but leave $H_2S$ unchanged when an $SO_2$ analyzer is employed to monitor $H_2S$ in a gas stream containing both gases. In order to effectively measure $H_2S$ with an $SO_2$ detector, an $H_2S$ to $SO_2$ converter is necessary. Stream switching is then employed to obtain the separate $H_2S$ and $SO_2$ concentrations. Other scrubber chemicals exist that will remove the $H_2S$ without affecting the $SO_2$ content. A further example is the use of an ozone scrubber to remove, otherwise toxic, ozone from the exhaust stream of a chemiluminescence NOx analyzer. The main advantage of scrubbers is that they almost all operate at room temperature whereas converters require an elevated and/or controlled temperature. On the other hand, scrubbers usually have a limited lifetime as the scrubber chemicals are consumed. Catalytic converters have a theoretically unlimited life which in practice is finite, due to slow poisoning of the catalyst. This selective conversion may preferably be accomplished using a catalyst, a thermal converter or a catalytic converter. Another preferable embodiment contemplates selective removal through combination of a scrubber and converter, either a catalyst, thermal converter, or catalytic converter may be employed as a converter. The catalyst is preferably present in a form where a large surface area is available. Some preferred forms include chips, turnings, wire, foil, screens, and or a series of screens. The catalyst is preferably a Group VIB transition metal, and an especially preferred catalyst is molybdenum. It is further preferable that the pressure drop through the selective removal step is between about 0 to about 10 inches of water, and more preferably less than one inch of water. Another preferred embodiment employs a selective removal step that is effective for removing the nitrogen-containing interferant to about a 90% to about a 100% removal, more preferably about 94% to about 100% removal and most preferably about 96% to about 100% removal. It is additionally preferable for the flow rate of the sample through the selective removal step to be about 400 to about 800 sccm, especially preferable is a flow rate of 650 sccm. During the cooling step, it is preferable for the sample to be cooled to ambient temperature within a period of about 0 to about 5 seconds, and more preferably within about 1 second.

Another embodiment of the present disclosure is an apparatus for measuring the concentration of a substance, for example a sulfur-containing species which may be combusted to form $SO_2$, that is effective for preventing interference due to nitrogen-containing interferants, for instance $NO_2$, in pyro-electrochemical techniques. A preferred embodiment includes a thermal oxidizer, where the sample containing a substance for analysis is volatilized under oxidation conditions, a removal device, where the removal device is effective for selectively removing the nitrogen-containing interferant from the sample, and a detector comprising one or more electrochemical cells capable of detecting the substance. The removal device may preferably be a scrubber, a device or material effective for selectively removing the interfering substance from the sample, or a converter, a device or material effective for selectively converting the nitrogen-containing interferant into a non-interfering species. The converter may preferably be a catalyst, a thermal converter, or a catalytic converter. Another preferred removal device utilizes a combination of a scrubber and a converter. The catalyst is preferably present in a form where a large surface area is available. Some preferred forms include chips, turnings, wire, foil, screens, and or a series of screens. The catalyst is preferably a Group VIB transition metal, and an especially preferred catalyst is molybdenum. It is especially preferred, when using chips or turnings, that the converter additionally comprise a catalyst retainer to hold the catalyst materials in place. Preferred catalyst retainers include stainless steel screens, molybdenum screens, quartz wool and permeable quartz plugs. A preferred optional feature of the thermal oxidizer is a temperature control device that is effective for controlling both the temperature of the thermal oxidizer and the removal device. An especially preferred embodiment utilizes a temperature control device to control the temperature of the removal device in an enclosure separate from that of the thermal oxidizer. A further preferred embodiment contemplates use of both the temperature control device of the thermal oxidizer and the temperature control device of the removal device in tandem to control the temperature of the removal device. An especially preferred feature of the removal device is that it is composed of a material that is inert to the sample gas and is also preferred to be capable of withstanding temperatures of up to about 550° C. The converter preferably operates at a temperature between about 300° C. and about 550° C., more preferably between about 350° C. to about 450° C., and the scrubber preferably operates at about or near room temperature. Some preferred materials are quartz and stainless steel, especially preferred are 316 stainless steel and 304 stainless steel. It is preferred for the removal device to comprise a housing, where the housing has a first and a second end cap. Some preferred dimensions of the housing include a housing that is about ½ inch outside diameter by about 1/16 inch wall thickness and where the housing is preferably between about 2 to about 6 inches long. The housing preferably includes an input and an output tube for effecting flow of the sample through the removal device. The input and output tubes are preferably about ¼ inch outside diameter by about 0.04 inch wall thickness and are preferably composed of stainless steel. Another preferable feature of the thermal oxidizer is that it is insulated. In addition, it is preferable that the removal device is also insulated. The removal device may preferably be either within the insulation surrounding the thermal oxidizer or contained within a separate insulated environment.

An additional preferred embodiment of the present disclosure contemplates an on-stream analyzer for measuring the concentration of a substance in a fluid sample where the analyzer has a sample injector, a thermal oxidizer, a converter, a sample conditioner, and a detector. It is preferred feature of the sample injector that it is effective for injecting the sample at a preset and controlled rate, and the sample injector may preferably include a pressure regulator coupled to a flow restrictor to control the rate of sample flow. It is preferred that the sample oxidizer include a tube furnace and a pyrolysis tube that is connected to the sample injector. The sample is preferably injected into the pyrolysis tube, volatilized, and mixed with a carrier and a pyrolysis gas, at a preset and controlled rate under oxidation conditions. It is preferred for the converter to selectively convert the nitrogen-containing interferant, such as $NO_2$, in the sample to a non-interfering species, like NO, by utilizing a molybdenum catalylst. It is a further preferred feature of the converter to comprise a housing, an input tube, and an output tube all composed of a material that is inert to the sample gas. Also, it is preferred for the sample conditioner, connected and located downstream from the converter and the thermal oxidizer, to control the conditions of the resulting gas mixture. The sample conditioner may optionally comprise a dryer, for removing water vapor, that has two concentric tubes, an inner tube preferrably composed of a membrane capable of transferring water vapor and an outer tube preferably composed of an inert material. In addition, it is preferable for the dryer to be configured so that a dry purge gas flows through the inner tube and the sample gas, to be dried, is directed through the annular space between the inner and outer tubes. The inner tube is preferably connected to a flow restrictor, with an orifice, capable of maintaining positive pressure within the tube. The detector, of the analyzer, may preferably comprise one or more electrochemical cells capable of measuring the concentration of the substance contained within the sample.

Another preferred embodiment of the present disclosure encompasses a method for detecting a substance, for example a sulfur-containing species which may be combusted to form $SO_2$, using pyro-electrochemical analyzer that involves the steps of providing a sample containing a substance for detection in a vapor state, controlling the flow rate of the sample as it progresses through the analyzer, thermally oxidizing the sample, selectively converting the interferant, for example $NO_2$, into a non-interfering species, such as NO, cooling the sample, conditioning the sample and detecting the substance. It is preferred for the sample injector to control the flow rate of the sample by utilizing a pressure regulator coupled to a flow restrictor. The use of a catalytic converter having a molybdenum catalyst is preferred to effectuate the selective conversion at about 300° C. to about 550° C., more preferably between about 350° C. to about 450° C. It is also preferable for the flow rate of the sample through the converter to be from about 400 sccm to about 800 sccm and preferably have a pressure drop through the converter of less than about 1 inch of water. Another preferred feature of the present disclosure involves a sample conditioning step effective to control the temperature and relative humidity of the sample. The temperature is preferably regulated with a heat trace element comprising self-limiting electrical heating wires and the relative humidity is preferably controlled by a dryer. The preferred embodiment of the dryer comprises two concentric tubes, an inner tube preferably composed of a ion-exchange membrane having sulfonic acid groups and an outer tube preferably composed of a fluoropolymer resin or stainless steel. The dryer is preferably arranged so that the dry purge gas is directed through the inner tube and the sample gas is directed through the annular space between the inner and outer tube. The inner tube is preferably connected to a flow restrictor having an orifice to maintain positive pressure. The cooling step preferably involves cooling the sample to ambient temperature within a period of about 0 to about 5 seconds and more preferably within about one second. The detection step is preferably accomplished with a detector having one or more electrochemical cells.

Another preferred embodiment of the present invention involves the detection of a substance for detection, for example sulfur-containing species which may be combusted to form $SO_2$, either by direct or indirect analysis. Such indirect analysis may be accomplished by detecting a constituent present in the sample to which the substance has been converted and then correlating the amount of that constituent to the amount of the substance prior to conversion.

DETAILED DESCRIPTION OF THE PREFERRED EMBODIMENTS

Figure 1:
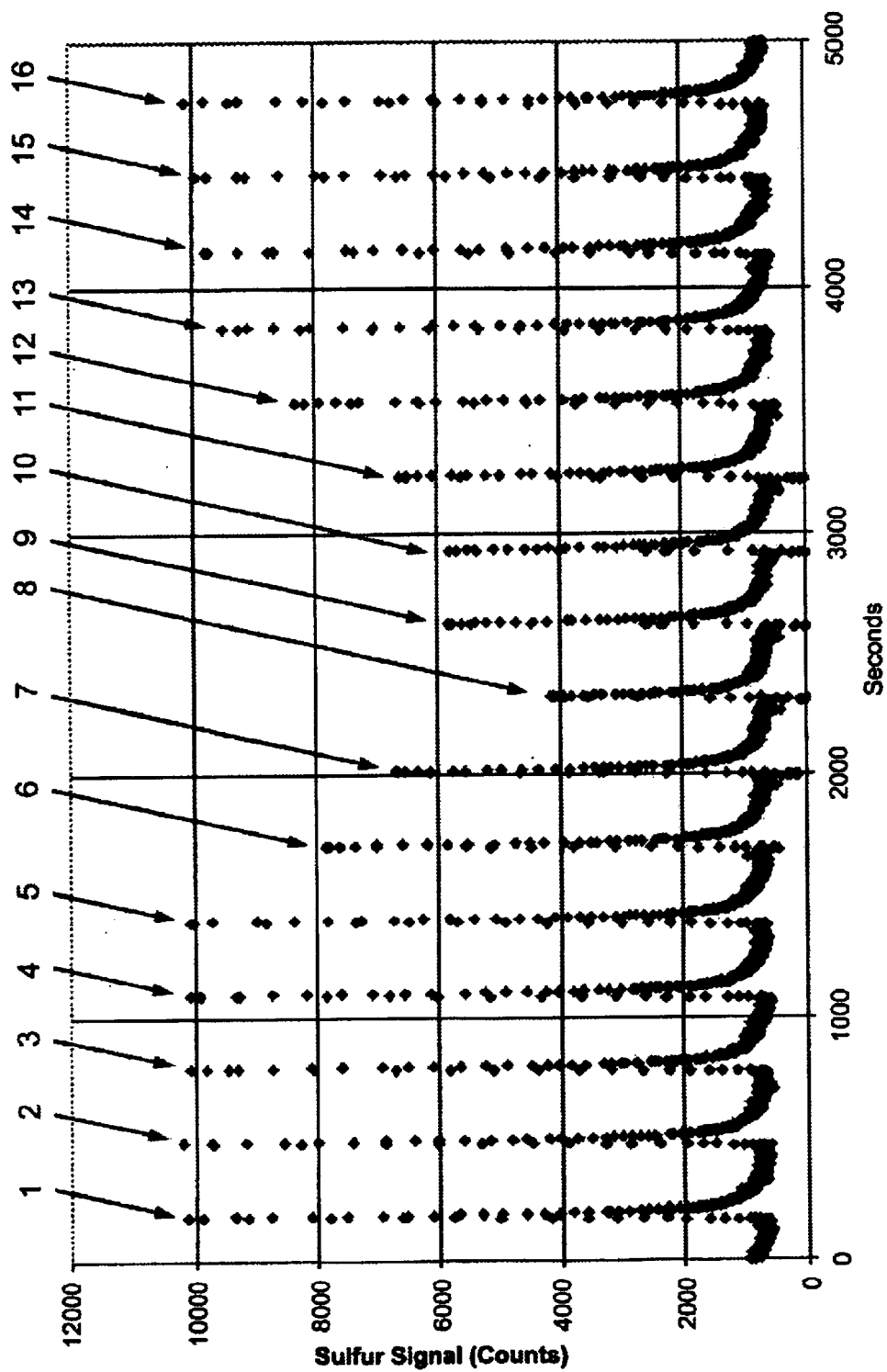
FIG. 1 is a graphical illustration of the typical effects of nitrogen interference.

FIG. 1 shows the results of measuring successive 20 microliter injections of diesel fuel, injected into the Pyrolysis Tube at 5 minute intervals and measured with an electrochemical $SO_2$ sensor. The area under each peak (and also the peak height since the peak shapes are similar to each other) is proportional to the sulfur signal. The first 5 injections, designated 1 through 5, are of a sample containing 20 ppm sulfur and zero nitrogen. It is seen that the sulfur signal is stable and repeatable. Between the fifth, 5, and sixth, 6, injections, the sample is changed to one containing 20 ppm sulfur and 50 ppm nitrogen. The sulfur signal is immediately reduced and part of it goes to zero and may be driven negative, injections #6 to #11, at 6 to 11. The effect becomes steadily worse even though the nitrogen content is constant. Between injection #8, 8, and #9, 9, the sample is switched back to 20 ppm sulfur with zero nitrogen. It is seen that it takes about 7 more injections, designated by 10 through 16, before the sensor fully recovers from the effects of the nitrogen.

An especially preferred converter type is catalytic because the temperature required is much lower than other methods and is within the range obtainable by burying the converter cartridge inside the pyrolysis furnace insulation. The preferred catalyst material is a Group VIB transition metal and more preferably molybdenum, which is known to operate well in the temperature range 300–550° C. Molybdenum is especially preferred because it is less likely to be oxidized by the enriched oxygen atmosphere of the pyrolysis exhaust than either copper or carbon, other potential catalysts and is less likely to react with $SO_2$.

Figure 2:
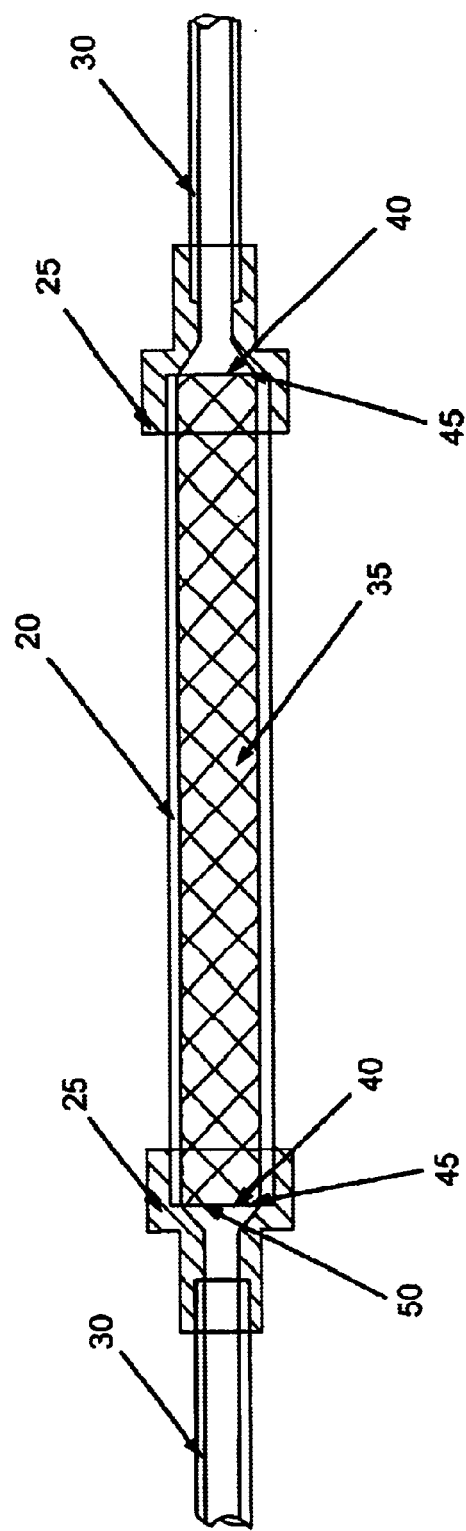
FIG. 2 is a section of a typical converter.

FIG. 2 shows a sketch of a typical converter. It is preferable for the materials wetted by the sample gas to be unreactive to $SO_2$ and capable of withstanding at least about 550° C. One preferred embodiment employs stainless steel or quartz. The pressure drop across the whole cartridge at the preferred sample flow rates of about 400 to about 800 sccm (standard cubic centimeters per minute) is preferably so small that extra back-pressure does not affect the quality of the pyrolysis upstream and any pressure fluctuations are preferably so small as to not affect the response of the electrochemical sensor downstream. One preferred embodiment aims for a pressure drop of less than about 1 inch of water at a gas flow of about 650 sccm. In another embodiment, the housing, 20, is about ½ inch outside diameter by 1/16 inch wall thickness stainless steel tubing 2 to 6 inches long. The end-caps, 25, are stainless steel Swagelok reducing unions, catalog number SS-810-6-4 (or equal). The input and output tubes, 30, are about ¼ inch outside diameter by about 0.040 inch wall thickness stainless steel tubing. The catalyst filling, 35, is either molybdenum wire, foil, mesh, screen, chips or turnings, or a series of molybdenum screens wedged in place, and preferably having suitable spacer rings. It is preferable that the chip size range or screen mesh size and spacing be selected so as to provide maximum surface area to the flowing gas without excessive pressure drop. The catalyst retainers, 40, preferred where the filling, 35, is chips or turnings, consist of stainless steel or molybdenum screens wedged into place between the housing ends, 45, and the unions, 50. It is preferable that the catalyst filling be such as to prevent "channeling" of the sample gas, for example, by settling of the chips to leave a gap (if the orientation of the converter is horizontal).

All materials wetted by the gas are preferably clean to avoid adsorption of $SO_2$ by, for example, oil films. A suitable cleaning process is to rinse in 1:1 HCl, then de-ionized water, then methanol, and allow to air dry at room temperature.

The converter is preferably placed inside the pyrolysis furnace, buried in the insulation at a location where the temperature is between about 300° C. and about 550° C. A typical commercially available tube furnace is about 8 inches outside diameter by about 12 inches long, with the center hole, on axis, about 1.5 inches in diameter. The heater is preferably coiled around the center hole and is controlled at about 1050° C. to provide this temperature along at least some of the length, for the pyrolysis tube that goes in the hole. The space between the heater coils and the outside enclosure is filled with ceramic fiber insulation.

Figure 3:
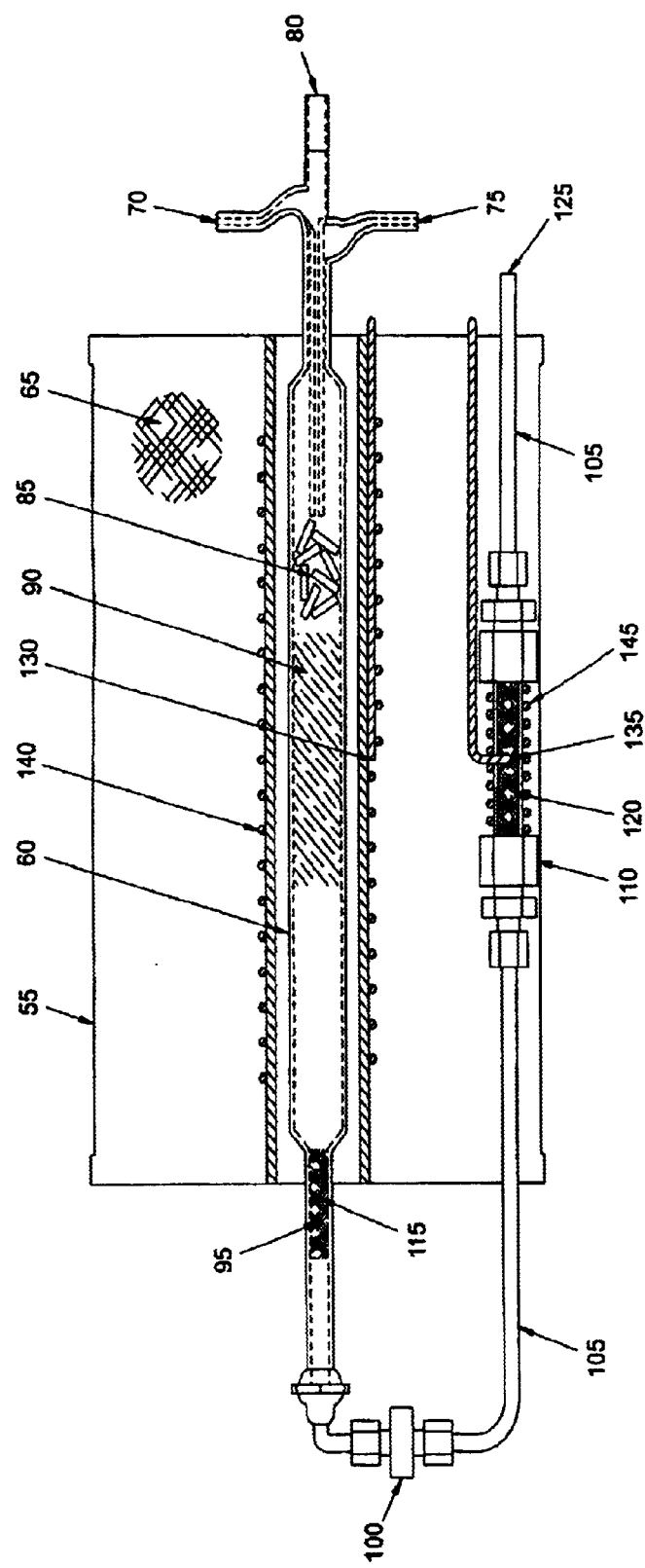
FIG. 3 is an illustration of a pyrolysis furnace in combination with a converter.

FIG. 3 shows a cylindrical pyrolysis tube furnace illustrating two preferred placements for the converter, at positions labeled 95 and 110. Item 55 is the cylindrical furnace outer casing; 60 is the quartz pyrolysis tube which is placed in the furnace tube; 65 is the ceramic fiber furnace insulation that fills the space between the furnace tube and the outer casing; 70 is the carrier gas inlet (in one preferred embodiment argon plus oxygen); 75 is the pyrolysis gas inlet (in one preferred embodiment, oxygen); 80 is the sample injector port, the sample injector port is connected to a sample injector that preferably injects the sample at a preset and controlled rate, a particularly preferred embodiment of the present disclosure utilizes a pressure regulator coupled to a flow restrictor to control the sample flow; 85 is the pyrolysis tube filling of small quartz tubules; 90 represents the pyrolysis temperature zone where the temperature is in the range of about 1000° C. to about 1050° C.; 100 is a particulate filter to prevent any soot or other particles from the pyrolysis migrating downstream; and may optionally include a sample conditioner, located downstream of the converter, where the sample conditioner preferably contains a dryer.

One preferred embodiment of the present disclosure utilizes a pressure regulator coupled to a flow restrictor to effectuate injection of the sample at a preset and controlled rate, as described in U.S. patent application Ser. No. 09/951,760, filed Sep. 11, 2001, and incorporated by reference herein. In one preferred embodiment the sample injection rate is controlled by is introducing an inert gas, such as argon or helium, at a constant pressure, via a pressure regulator, to a flow restrictor such as a length of capillary tubing or a micro-metering valve. The gas, thus flowing at a constant rate, pushes the liquid sample out of a fixed volume sample loop or other sample measuring device, through an injector tube and into the pyrolyzer. When using a length of capillary tubing, a diameter between about 0.001 to about 0.020 inches is preferable. Another especially preferred embodiment of the flow restrictor employs a micrometering valve capable of flow rates of less than 1 $\mu$l/s. The flow rate may be calibrated prior to operation using a bubblemeter and stopwatch or by timing the appearance and development of the liquid sample drop at the injector tip with the injector out of the pyrolyzer.

A further preferred embodiment makes use of a sample conditioner connected to and located downstream from the pyrolysis furnace and the converter. The sample conditioner controls the conditions of the resulting gas mixture and is described in U.S. patent application Ser. No. 09/951,760, filed Sep. 11, 2001, and incorporated by reference herein. The sample conditioner preferably includes one or more of the following, a filter, a dryer, and/or a heat trace element. The filter is preferably made of a chemically inert material, such as polytetrafluorethylene or metal screen, preferably stainless steel, and prevents solid particles or liquid drops from passing downstream thereby preventing contamination of downstream components and/or surfaces. The heat trace element is preferably composed of self-limiting electrical heating wires that are effective to maintain the gas stream above its dewpoint from the pyrolysis tube to the dryer. The dryer preferably contains two concentric tubes, an inner tube and an outer tube. The inner tube composed of a membrane for transferring water vapor, preferably the membrane contains active groups for effectuating the water transfer and the active groups are preferably sulfonic acid groups interspersed within the membrane. One preferable embodiment includes a perfluorinated membrane with sulfonic acid groups such as a NAFION membrane. The outer tube is composed of an inert material that is preferably a fluoropolymer or stainless steel. It is further preferable for the dryer to be configured so that a dry purge gas passes through the inner tube and the sample gas is directed through the annular space between the outer tube and the inner tube. Further, the dryer may optionally contain a restrictor, connected to the inner tube to maintain positive pressure within the dryer. The restrictor preferably includes an orifice having a diameter of about 0.001 inches to about 0.05 inches, preferably 0.0122 inches.

Item 110 is one preferred zone for placement of the converter material, where the temperature range is between about 300° C. to 550° C. This embodiment achieves a preferred temperature by placing the converter at about ½ to about 1 inch inside the outer wall of the furnace enclosure, on a horizontal radius out from the heater coil and centrally located axially. Item 105 is the inlet and outlet tubing to this embodiment of the converter, and comprises stainless steel or quartz; 110 is the converter; 120 is the converter filling; 125 is the sample gas outlet to the sample dryer and detector subassemblies and other components as necessary (such as a programmable logic controller for calculating data obtained from the detector) for the on-line pyro-electrochemical analyzer; 130 is the furnace thermocouple used for furnace temperature sensing, control and alarming; 135 is the converter thermocouple used for sensing, control and alarming the converter temperature; 140 is the electrical heater for the pyrolysis tube furnace; and 145 is the electrical heater for the converter cartridge. Another preferred placement is shown in the exhaust portion of the quartz pyrolysis tube, 95, where the temperature is in the proper range, between about 300° C. to about 550° C. In this case, the converter material, 115, is preferably molybdenum wire, suitably coiled to provide maximum surface area to the gases and minimum pressure drop.

Note that the catalytic converter may also be housed in a separate temperature-controlled, insulated enclosure.

Figure 4:
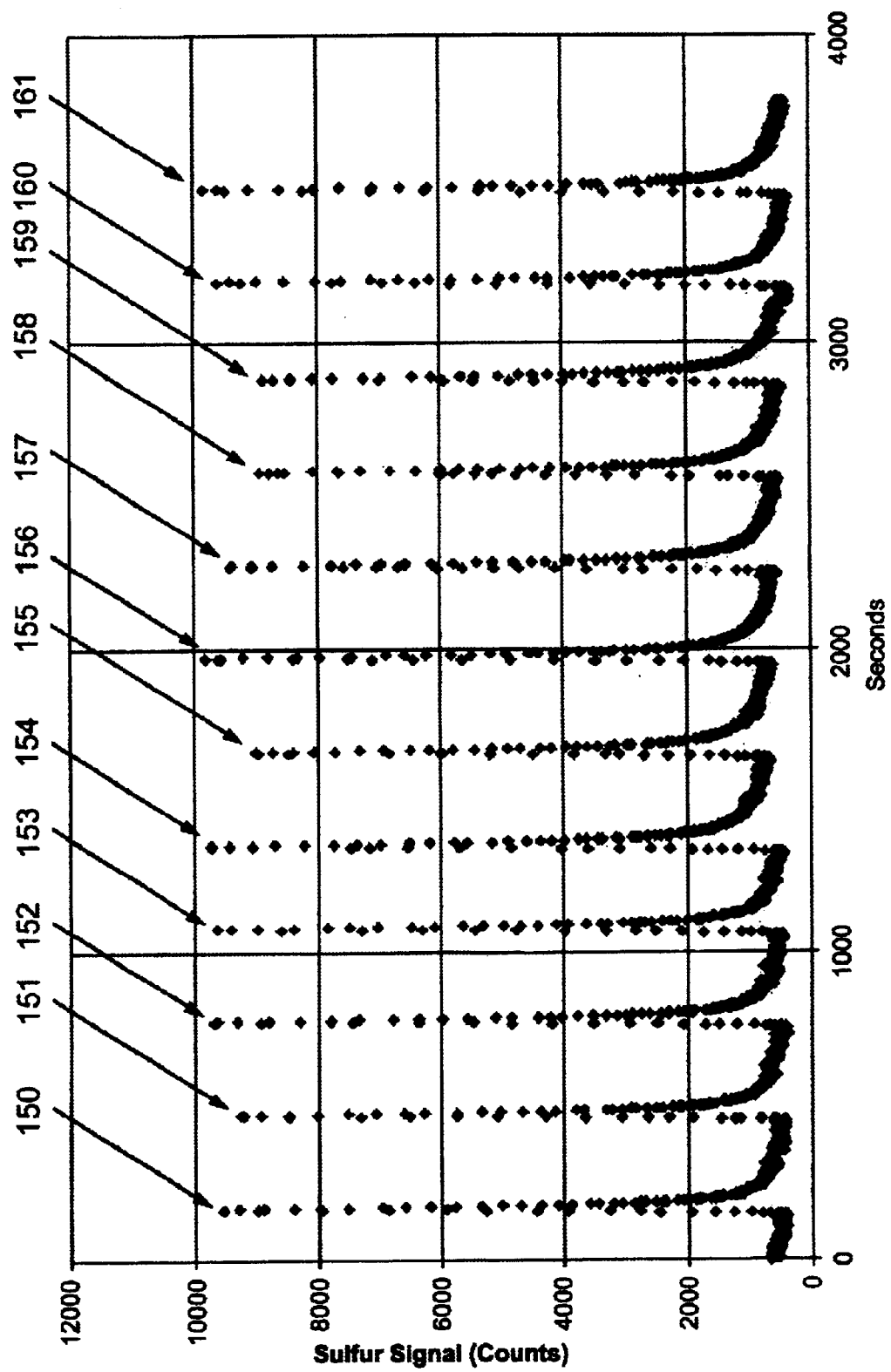
FIG. 4 is a graphical illustration of the typical effects when a converter is used.

Performance tests of this converter are shown in FIG. 4, where samples containing 20 ppm sulfur and either zero or 50 ppm nitrogen were analyzed, just as in FIG. 1. As before, successive 20 microliter injections of sample into the pyrolysis tube are made at 5-minute intervals, designated by numbers 150 through 161. The height of each signal peak is proportional to the electrochemical sulfur dioxide signal. The first three injections, 150 through 152, are of 20 ppm sulfur, zero ppm nitrogen in diesel fuel and are made without the converter installed. The converter is then installed between the third, 152, and fourth, 153, injections. The signal does not change, indicating that the $SO_2$ content is unaffected by the converter. The sample is changed to 20 ppm sulfur, 50 ppm nitrogen between injections #5, 154, and #6, 155. The sulfur signal remains unchanged (except for some instability caused by the experimental procedure). The sample is then changed back to 20 ppm sulfur, zero nitrogen between injections #9, 158, and #10, 159. Again the sulfur signal is essentially unaffected. It is seen that the sulfur signal remains steady both before and after the converter is installed, and with or without 50 ppm nitrogen in the samples. This verifies a) that $NO_2$ is being produced during or immediately after pyrolysis, b) that the converter does not react significantly with $SO_2$, c) that the molybdenum converter is converting a significant portion of $NO_2$ back to NO and d) that the chemical reaction is effectively "frozen" after the gases exit the converter.

Preferably, the scrubber effectively removes the $NO_2$ from the sample while not affecting the $SO_2$ concentration and preferably operates at or near room temperature. It is also preferable that the active chemical of the scrubber not react significantly with any other gas present, such as the $O_2$, $CO_2$ or water vapor. If water vapor affects the scrubber chemical, it is preferable for the scrubber to be located downstream of the dryer, which is already present as a preferred embodiment of the pyro-electrochemical analyzer.

Selection of a chemical that satisfies the criteria of reacting with $NO_2$ yet being inert to other gases in the stream, especially $SO_2$, may be difficult. There are numerous chemicals that satisfy the criteria set forth herein, the selection of which is within the skill of one in the art, and each are contemplated by the present disclosure.

Figure 5:
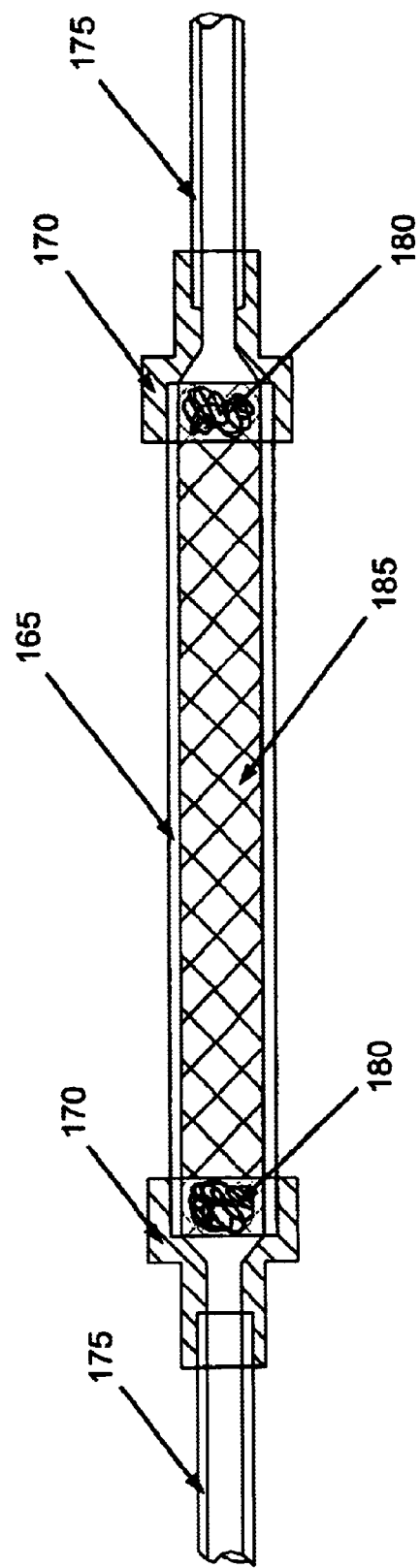
FIG. 5 is a section of a scrubber.

FIG. 5 shows a sketch of a typical scrubber cartridge. Pressure drop requirements are the same as for the converter cartridge, although the scrubber is preferably designed to operate at or near room temperature. In one embodiment, the housing, 165, is preferably about ½ inch outside diameter by about 1/16 inch wall thickness, composed of a fluoropolymer, for example "TEFLON", or stainless steel tubing 2 to 6 inches long. The end-caps, 170, are preferably stainless steel or a fluoropolymer reducing unions. The input and output tubes, 175, are preferably about 1/4 inch outside diameter by about 1/16 inch wall thickness and composed of a fluoropolymer or stainless steel tubing. The filling, 185, preferably consists of the active chemical deposited from solution on an inert support, is preferably porous, and preferably has a large surface area. Some preferred support materials include turnings or shavings of porous fluorcarbon polymer, or pieces of fluorcarbon membrane filter. The filling is preferably packed so as to prevent channeling, to preferably provide maximum surface area to the flowing gas stream and to preferably avoid excessive pressure drop. The retaining plugs, 180, are preferred where the filling requires them, and are preferably quartz wool although any suitable inert, porous material may be utilized. All materials wetted by the gas are preferably clean so as to avoid any adsorption of $SO_2$ by, for example, oil films. A suitable cleaning process for the tubing and fittings is to wipe with methanol and allow to air dry at room temperature.

What is claimed is:

1. An apparatus for measuring the concentration of a substance in a nitrogen-containing sample and effective in removing nitrogen interference in pyro-electrochemical methods comprising:
   a. a thermal oxidizer to form an oxidized substance;
   b. a converter, wherein said converter is effective for selectively converting the $NO_2$ in a sample to NO, and wherein the converter is a catalytic converter having a molybdenum catalyst, and wherein said converter further comprises a housing and an input and an output tube, and wherein said converter is composed of a material that is inert to the sample gas; and
   c. a detector, wherein the detector comprises an assembly of one or more electrochemical cells capable of detecting the oxidized substance.

2. The apparatus of claim 1, wherein the converter operates at a temperature between about 300° C. to about 550°.

3. The apparatus of claim 1, wherein the thermal oxidizer additionally comprises a temperature control device, the temperature control device being effective for controlling the temperature of the converter.

4. The apparatus of claim 1, wherein the converter additionally comprises a temperature control device.

5. The apparatus of claim 1, wherein the thermal oxidizer is insulated, and further wherein the converter is insulated.

6. The apparatus of claim 1, wherein the converter is located in a temperature controlled enclosure separate from that of the thermal oxidizer.

7. An on-stream analyzer for measuring the concentration of a substance in a nitrogen-containing fluid sample, said analyzer comprising:
   a. a sample injector for injecting the sample at a preset and controlled rate, the sample injector further comprising a pressure regulator coupled to a flow restrictor to control the rate of sample flow;
   b. a thermal oxidizer, to form an oxidized substance, comprising a tube furnace and a pyrolysis tube, connected to the sample injector;
   c. a converter, wherein said converter is effective for selectively converting the $NO_2$ in a sample to NO, and wherein the converter is a catalytic converter having a molybdenum catalyst, and wherein said converter further comprises a housing and an input and an output tube, and wherein said converter is composed of a material that is inert to the sample gas;
   d. a sample conditioner, connected to and located downstream from the thermal oxidizer, to control the conditions of a resulting gas mixture; and
   e. a detector, connected to the sample conditioner, to measure the concentration of an oxidized substance contained within the gas mixture.

8. An on-stream analyzer for detecting a substance in a nitrogen-containing fluid sample, said analyzer comprising:
   a. a fluid sample injector;
   b. a thermal oxidizer, connected to the sample injector, wherein the sample is injected into the thermal oxidizer and a carrier gas and a pyrolysis gas are introduced to the sample under oxidation conditions to form an oxidized substance
   c. a converter, wherein said converter is effective for selectively converting the $NO_2$ in a sample to NO, and wherein the converter is a catalytic converter having a molybdenum catalyst, and wherein said converter further comprises a housing and an input and an output tube, and wherein said converter is composed of a material that is inert to the sample gas;
   d. a sample conditioner, connected to the thermal oxidizer, to control the conditions of a resulting mixture, wherein the conditioner further comprises a dryer for removing water vapor, wherein the dryer further comprises two concentric tubes, an inner tube composed of a membrane for transferring water vapor and an outer tube composed of an inert material, wherein the dryer is configured to operate so that a dry purge gas is directed through the inner tube and the sample gas is directed through the annular space between the inner and outer tube, and further wherein the inner tube is connected to a flow restrictor having an orifice to maintain positive pressure; and
   e. one or more electrochemical cells, connected to the sample conditioner, to measure the concentration of the oxidized substance contained within the sample.

9. A method for detecting a substance in a sample comprising the steps of:
   a. providing a nitrogen-containing sample in vapor state;
   b. controlling the flow rate of the sample using a pressure regulator coupled to a fixed flow restrictor;
   c. thermally oxidizing the sample to form an oxidized substance;
   d. selectively converting $NO_2$ in the sample to NO, wherein the selective conversion step is accomplished using a catalytic converter having a molybdenum catalyst, from about 300° C. to about 550° C., and wherein the flow rate through the catalytic converter is about 400 to about 800 sccm, and further wherein the pressure drop through the catalytic converter is less than about 1 inch of water;
   e. cooling the sample, wherein the sample is cooled to ambient temperature within about one second after the selective conversion; and
   f. detecting the oxidized substance within the sample.

10. A method for detecting a substance in a sample comprising the steps of:
   a. providing a nitrogen-containing sample in vapor state;
   b. thermally oxidizing the sample to form an oxidized substance;
   c. conditioning the sample to control the temperature and relative humidity of the sample, wherein the temperature is regulated with a heat trace element comprising self-limiting electrical heating wires and wherein the relative humidity is controlled by a dryer comprising two concentric tubes, an inner tube composed of a ion-exchange membrane having sulfonic acid groups and an outer tube composed of a fluoropolymer resin or stainless steel, wherein a dry purge gas is directed through the inner tube and the sample gas is directed through the annular space between the inner and outer tube, and further wherein the inner tube is connected to a flow restrictor having an orifice to maintain positive pressure;

d. selectively converting $NO_2$ in the sample to NO, wherein the selective conversion step is accomplished using a catalytic converter having a molybdenum catalyst, from about 300° C. to about 550° C., and wherein the flow rate through the catalytic converter is about 400 to about 800 sccm, and further wherein the pressure drop through the catalytic converter is less than about 1 inch of water;

e. cooling the sample, wherein the sample is cooled to ambient temperature within about one second after the selective conversion; and f. detecting the oxidized substance within the sample.

* * * * *

UNITED STATES PATENT AND TRADEMARK OFFICE
CERTIFICATE OF CORRECTION

PATENT NO. : 6,867,047 B2
DATED : March 15, 2005
INVENTOR(S) : John R. Rhodes

It is certified that error appears in the above-identified patent and that said Letters Patent is hereby corrected as shown below:

<u>Column 1,</u>
Line 18, delete "analysis if a substance" please insert -- analysis of a substance --.

<u>Column 2,</u>
Line 17, delete "contact with." please insert -- contact. --.

Signed and Sealed this

Twenty-fourth Day of May, 2005

JON W. DUDAS
*Director of the United States Patent and Trademark Office*